United States Patent [19]

Umezawa et al.

[11] Patent Number: 4,550,021
[45] Date of Patent: Oct. 29, 1985

[54] ANTITUMOR ANTIBIOTIC 81-484 AND PROCESS FOR ITS PRODUCTION

[75] Inventors: Iwao Umezawa, Tokyo; Kanki Komiyama, Yokohama, both of Japan

[73] Assignee: The Kitasato Institute, Tokyo, Japan

[21] Appl. No.: 617,470

[22] Filed: Jun. 5, 1984

[30] Foreign Application Priority Data

Dec. 28, 1983 [JP] Japan ............................... 58-245572

[51] Int. Cl.$^4$ ......................... A61K 35/74; C12P 1/06
[52] U.S. Cl. .................................... 424/122; 435/169
[58] Field of Search ......................... 424/122; 435/169

[56] References Cited

U.S. PATENT DOCUMENTS 4,279,894 7/1981 Davies et al. ...................... 424/122
4,283,390 8/1981 Koch et al. ......................... 424/122

*Primary Examiner*—Jerome D. Goldberg
*Attorney, Agent, or Firm*—Young & Thompson

[57] ABSTRACT

Antibiotic 81-484 of the following physico-chemical properties:

(1) elementary analysis: $C_{33}H_{48}O_7$ (high resolution mass spectrum);
(2) molecular weight: 556 [Field desorption (FD) mass spectrum];
(3) melting point: not clear (oily at 10°-100° C.);
(4) specific rotation: $[\alpha]_D^{20} = -151°$ (c=0.1, methanol);
(5) ultraviolet absorption spectrum: shown in FIG. 1 (in methanol);
(6) infrared absorption spectrum: shown in FIG. 2 (KBr tablet);
(7) solubility: insoluble in hexane and water, soluble in diethyl ether, methanol, ethanol, dichloromethane, chloroform, ethyl acetate, butyl acetate, acetone and benzene;
(8) nuclear magnetic resonance spectrum: shown in FIG. 3 ($CDCl_3$, TMS);
(9) nature: acidic substance;
(10) color reaction:
negative for ninhydrin, anthrone-$H_2SO_4$ and ferric chloride reaction;
positive for iodine and antimony trichloride;
weakly positive for Zatkis reagent;

or a non-toxic salt thereof, is produced by culturing *Streptomyces* 81-484 FERM-P 7371 in a culture medium, and isolating the thus-produced antibiotic therefrom. The antibiotic has no antibiotic activity against Gram-positive and -negative bacteria, has antimicrobial activity against some kinds of fungi, and has growth inhibitory activity against P388 mouse leukemia cells and sarcoma 180 cells.

1 Claim, 3 Drawing Figures

ANTITUMOR ANTIBIOTIC 81-484 AND PROCESS FOR ITS PRODUCTION

This invention relates to a novel antitumor antibiotic 81-484 and to a process for the production thereof. More particularly the present invention pertains to antibiotic 81-484 which is produced by culturing an antibiotic-81-484-producing microorganism belonging to genus Streptomyces, having no antibiotic activity against Gram-positive and -negative bacteria, having antimicrobial activity against some kinds of fungi, and having growth inhibitory activities against P388 mouse leukemia cells and Sarcoma 180 cells, or a non-toxic salt thereof, and a process for the production thereof.

We have found that a strain 81-484 isolated from a soil sample collected in Chiba-prefecture, Japan, produces an antibiotic substance showing antimicrobial activity against P388 mouse leukemia and sarcoma 180 cells. The said antibiotic substance has been isolated from the cultured mass and purified and has been found to possess novel physico-chemical properties. The said substance is referred to by us as antibiotic 81-484.

An object of the present invention is to provide a novel antibiotic 81-484 or a non-toxic salt thereof.

Another object of the present invention is to provide a process for the production of antibiotic 81-484 or a non-toxic salt thereof, which comprises culturing an antibiotic-81-484producing microorganism belonging to genus Streptomyces in a medium to accumulate the antibiotic 81-484 and isolating the antibiotic 81-484 therefrom, and if required converting the said antibiotic to a non-toxic salt thereof.

The antibiotic-81-484-producing microorganism belongs to genus Streptomyces, and the strain 81-484 belonging to genus Streptomyces isolated by the inventors of the present invention is illustrative only.

The taxonomical properties of the said strain 81-484 are as follows:

A. Morphological properties:

Strain 81-484 grows abundantly filamentous on many agar plate media. Dissection of substrate mycelia is not observed. When aerial mycelia are formed, the sporangiophore is straight or loose incomplete spirals with spore chains of more than 20 spores at the top thereof, and no sporangia are observed. The surface of spore is smooth and ellipsoidal, 0.8 μm along the major axis×0.4 μm along the minor axis.

B. Growth conditions on various media at 27° C. for 3 weeks' culture are as follows:

| Medium | Growth | Color of reverse | Color of surface of aerial mycelia | Soluble pigment |
|---|---|---|---|---|
| yeast-malt agar (ISP M2) | good | pastel-yellow (1½ fb) | ivory (2db) | wheat (2fb) |
| oatmeal agar (ISP M3) | almost no growth | — | — | — |
| starch-inorganic salt agar (ISP M4) | restricted growth | ivory (2db) | ivory (2db) | ivory (2db) |
| glycerin-asparagine agar (ISP M5) | good | yellowish-gray (2ca) | brownish-white (3ca) | brownish ish white (3ba) |
| peptone-yeast-iron agar (ISP M6) | restricted growth | pale yellow-orange (3ea) | pale yellow-orange (3ea) | (2hb) |
| tyrosine agar (ISP M7) | good | light brownish gray (3ec) | light grayish-yellow brown (2ie) | light brown-ish gray (2ec) |

Culturing is performed according to the method of the ISP (International Streptomyces Project). Color is determined by consulting the "Color Harmony Manual" (4th Ed.) Wilhelm Ostwald.

C. Physiological properties:

1. Growth temperature: grown at 20°–37° C., and at 27° C. for optimum growth.
2. Liquefaction of gelatin (glucose-peptone-gelatine medium): negative.
3. Hydrolysis of starch (starch-inorganic agar medium): negative.
4. Coagulation and peptonization of skim milk (10% skim milk medium: negative for coagulation; positive for peptonization.
5. Formation of melanin pigment (tyrosine agar medium and peptone-yeast-iron agar medium): negative.
6. Formation of $H_2S$ (peptone-yeast-iron agar medium): negative.
7. Formation of sulfite (sulfate medium): positive.

D. Assimilation of carbon sources: (observed on Pridham-Gottlieb agar medium at 27° C. for one month; ++: good utilization, +: utilization, —: non-utilization):

L-arabinose —
D-xylose —
D-glucose ++
D-fructose —
sucrose —
inositol +
L-rhamnose +
raffinose —
D-mannitol —

E. Composition of cell wall:

(Method according to Becker, et al. [Appl. Microbiol., 13, 236-243 (1965)]: LL-type diaminopimeric acid.

According to the taxonomical properties hereinabove, the strain 81-484 belongs to genus Streptomyces. The exact species of this strain has not been elucidated, and so is referred to by us as Streptomyces 81-484. This strain has been deposited in The Fermentation Institute, Agency of Industrial Science and Technology, M.I.T.I., Japan and assigned No. FERM-P 7371.

In general, the taxonomical properties of Streptomyces are easily to mutate, and so natural or artificial mutation derived from conventional mutation techniques, for example ultraviolet or X-ray irradiation, or treatment with mutagen such as N-methyl-N-nitro-N-nitrosoguanidine or ethylmethane sulfonate can easily be used. Those natural and artificial mutants that belong to genus Streptomyces and that have antibiotic-81-484-producing activity can be used in the present invention.

In the process of the present invention, an antibiotic-81-484-producing microorganism belonging to genus Streptomyces, preferably Streptomyces 81-484 FERM-P 7371, is cultured in a suitable medium for Streptomyces.

Any nutrient medium containing assimilable carbon and nitrogen sources and, if required, inorganic salts can be used. Examples of assimilable carbon sources are glucose, molasses, starch, dextrin, cellulose, glycerin or organic salts. These are used in combination or individually. Examples of assimilable nitrogen sources are organic nitrogen sources such as peptone, meat-extract, yeast-extract, dry yeast, soybean powder, corn steep liquor, cotton seed oil, casein, soybean protein hydrolysate, amino acid and urea or inorganic nitrogen sources such as nitrates and ammonium salts. If necessary, inorganic salts of sodium, potassium, calcium or magnesium, as phosphates, can be used. Furthermore, if required, trace nutrients, growth stimulants or precursors of antibiotic 81-484 can optionally be added to the medium.

Cultivation is carried out, in general, by shaking culture or aeration agitation culture. Submerged aeration culture is preferable for industrial production. The pH of the medium is preferably neutral. The culturing temperature is 20°-37° C., generally 24°-30° C., and preferably 27° C. The culturing time is usually 4-6 days for liquid culture. Cultivation can preferably be stopped at maximum antibiotic production in the medium. These culturing conditions, such as temperature, agitation, aeration and other culturing conditions, should naturally be controlled depending upon the nature of individual strains. An anti-foaming agent such as silicone oil, vegetable oil or a surface active agent can be added to prevent foaming.

Antibiotic 81-484 is mainly accumulated in the culture filtrate, and so the cultured mass is filtered with the aid of a filter-aid such as Celite or Hyflo-supercel (trade names), or centrifuged to separate the mycelia and filtrate wherefrom the antibiotic is preferably isolated.

The antibiotic 81-484 is also found in mycelia, and is isolated by extracting with methanol or acetone, concentrating in vacuo the said extract and purifying it in the same way as isolation from the filtrate.

Since the antibiotic 81-484 is insoluble in hexane and water, and soluble in many types of organic solvent, for example alcoholic solvents such as methanol or ethanol, chloroform-type solvents such as dichloromethane or chloroform, or ketone-type solvents such as acetone or methyl isobutyl ketone, and is acidic in nature, purification is effected by making use of these natures. In general, the culture filtrate is extracted with a water-immiscible organic solvent such as chloroform, methyl isobutyl ketone, ethyl acetate or butyl acetate to transfer the antibiotic into the organic solvent. For extraction, the culture filtrate is preferably adjusted to pH 3.0-5.0 initially.

The organic solvent layer is optionally washed with an aqueous solution of ethylenediamine tetraacetate for removing metallic ions, and is dehydrated by adding a dehydrating agent such as anhydrous sodium sulfate, anhydrous magnesium sulfate or a beads gel. The dehydrated organic solvent layer is concentrated in vacuo. Although antibiotic 81-484 is stable under heating, concentration is preferably carried out below 60° C. Hexane or petroleum ether is added to the concentrate to precipitate the antibiotic 81-484. The thus-obtained precipitate is washed with hexane and purified by filtration and centrifugation, whereupon antibiotic 81-484 is obtained as crude brownish-colored substance.

Further purification is carried out by making use of the difference in solubility of antibiotic 81-484 and the contaminants, the difference in distribution ratio for an immiscible tow-liquid-phase system, or differential adsorption. Preferable purification methods are chromatography, for example adsorption chromatography using an adsorption resin such as silica gel, alumina, activated cellulose or hydroxyappatite HP-20, reverse phase partition chromatography using silanated silica gel or octadecylsilanated silica gel, molecular sieve gel-filtration chromatography using Sephadex LH-20 or Toyopearl (trade names), or ion-exchange chromatography using DEAE-cellulose, DEAE-Sephadex or DEAE-Toyopearl (trade names).

Thus antibiotic 81-484 can be purified by using any of these techniques of chromatography, electrophoresis, counter-current distribution, ultrafiltration or distillation, or others, individually or in combination in a selected series thereof. For example, the crude substance, dissolved in a small amount of chloroform or benzene, is adsorbed in a packed silica-gel column, and is chromatographed with a hexane-acetone mixture. The active fractions are collected and concentrated in vacuo. The concentrate, dissolved in a small amount of chloroform, is adsorbed in a silica gel column and chromatographed with a mixed solvent of chloroform-methanol. The active fractions are collected and concentrated in vacuo. The concentrate dissolved in a small amount of methanol, is again chromatographed by adsorbing with a reverse phase silica gel column and eluting with a methanol-water mixture to purify the antibiotic 81-484.

Antibiotic 81-484 is an acidic substance and can be prepared as a salt thereof by any known process. The salts are pharmacologically acceptable non-toxic salts, for example an alkali metal salt such as sodium or potassium, an alkaline earth metal salt such as calcium or magnesium, or a conventional salt with an organic amine.

The physico-chemical and biological properties of antibiotic 81-484 are as follows:

A. Physico-chemical properties:

1. Properties: colorless or pale yellowish viscous oily material.

2. Elemental formula: $C_{33}H_{48}O_7$ (high resolution mass-spectrum).

3. Molecular weight: 556 (field desorption mass-spectrum).

4. Melting point: no clear melting point (oily at 10°-100° C.).

5. Specific rotation: $[\alpha]_D^{20} = -151°$ (c=0.1, methanol).

Figure 1:
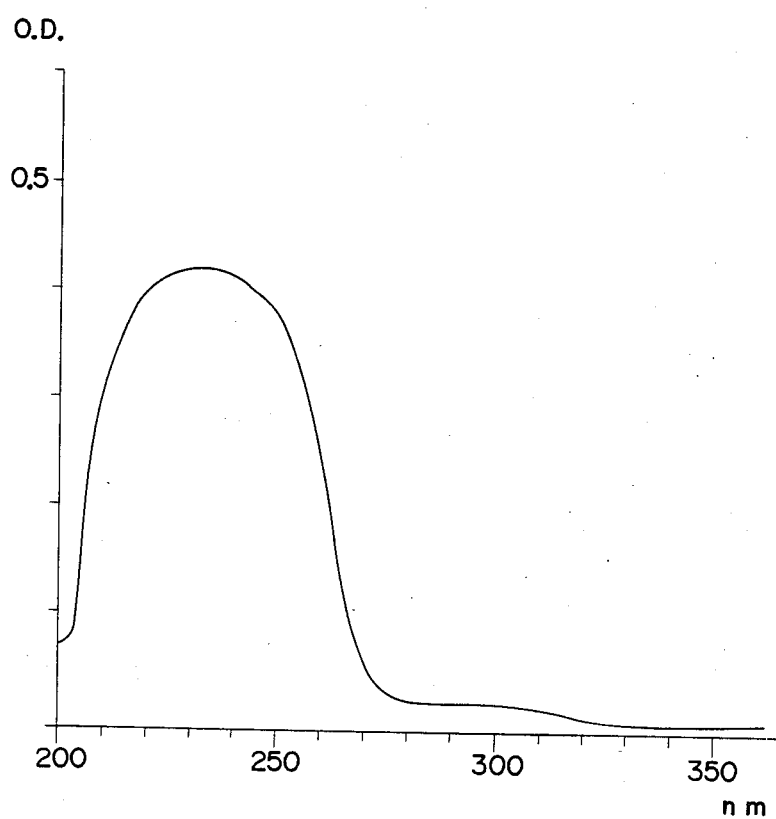
FIG. 1 is the UV spectrum of antibiotic 81-484.

6. Ultraviolet absorption spectrum: shown in FIG. 1 (in methanol).

Figure 2:
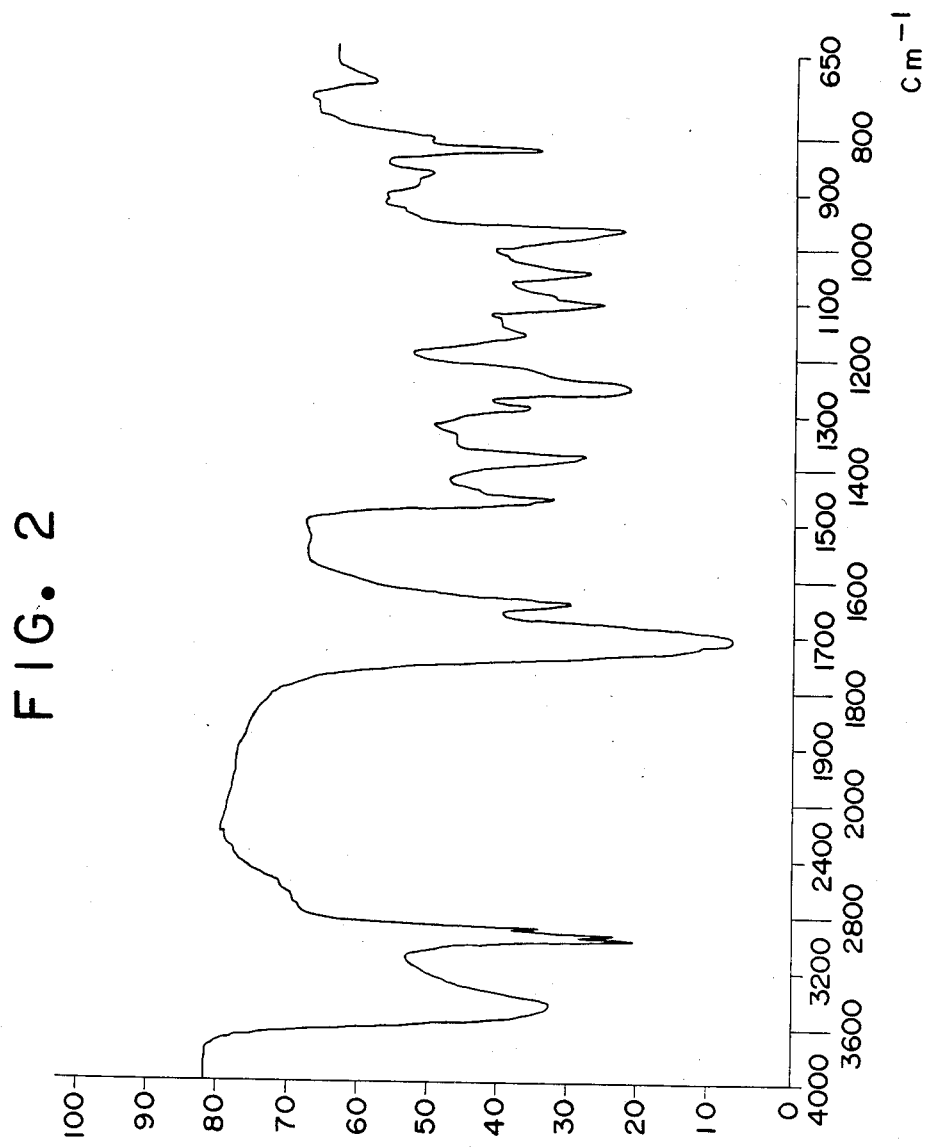
FIG. 2 is the IR spectrum of antibiotic 81-484.

7. Infrared absorption spectrum: shown in FIG. 2 (KBr tablet).

8. Solubility: insoluble: hexane, water; soluble: diethyl ether, methanol, dichloromethane, chloroform, ethyl acetate, butyl acetate, acetone, benzene.

Figure 3:
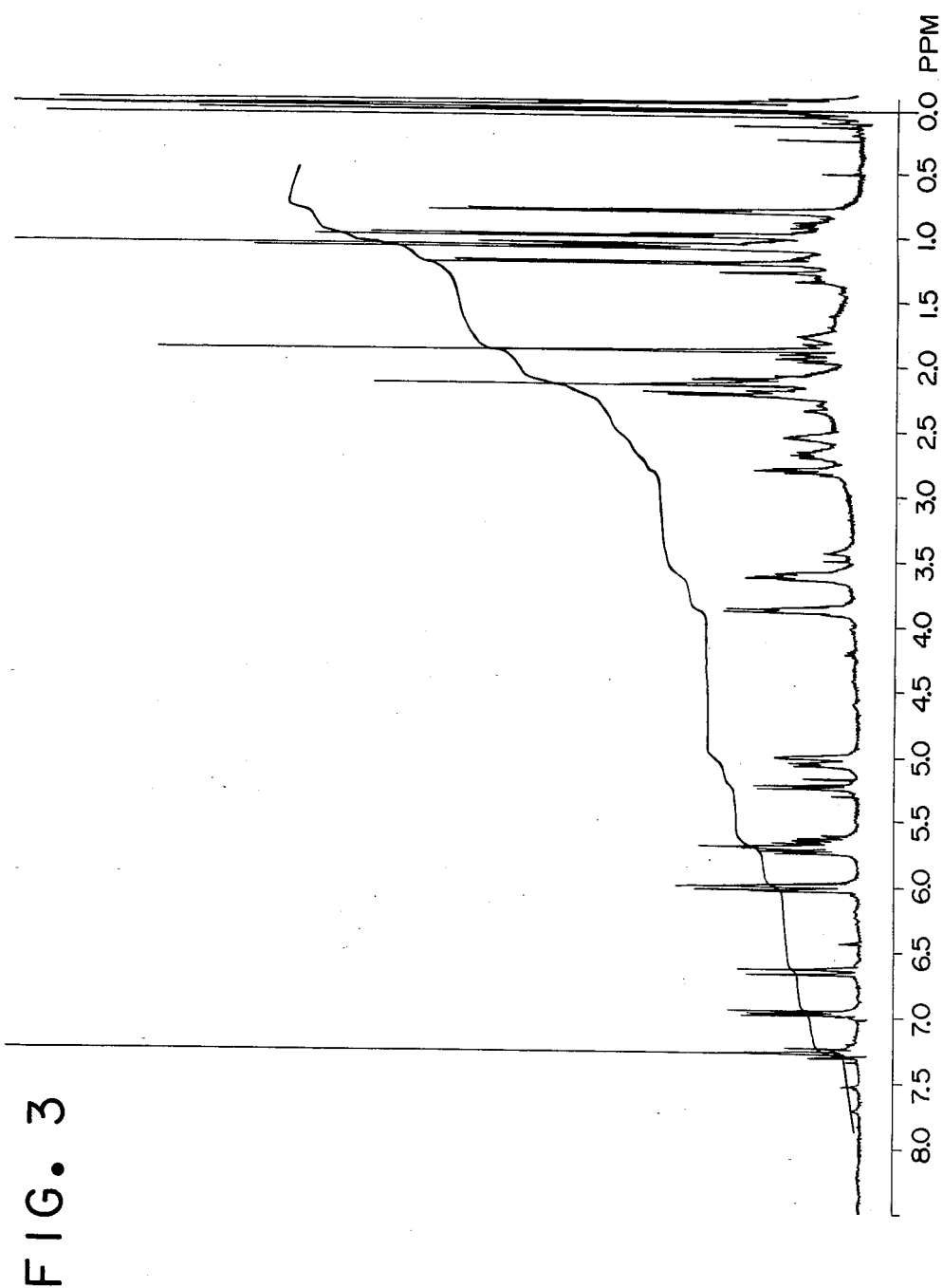
FIG. 3 is the NMR spectrum of antibiotic 81-484.

9. Nuclear magnetic resonance spectrum: shown in FIG. 3 (400 Hz, $CDCl_3$, TMS)

10. Nature: acidic substance.

11. Color reaction: negative: ninhydrin, anthrone-$H_2SO_4$, ferric chloride; positive: iodide, antimony trichloride; weakly positive: Zatkis reagent.

12. Silica gel thin layer chromatography: (carrier: silica gel 60, Merck) Rf=0.33 (ethyl acetate:methanol=40:1) Rf=0.28 (chloroform:methanol=10:1).

B. Biological properties:

1. Antimicrobial spectrum:

| Test organisms | MIC (g/ml) |
| --- | --- |
| *Staphylococcus aureus* FDA 209P | >50 |
| *Bacillus subtilis* PCI 219 | >50 |
| *Sarcina lutea* PCI 1001 | >50 |
| *Escherichia coli* NIHJ | >50 |
| *Shigella sonnai* | >50 |
| *Saccharomyces sake* | >50* |
| *Candida albicans* | >50* |
| *Schizosaccharomyces pomb* IAM 4803 | 0.1** |
| *Trichophyton ferginium* | >50** |

MIC = minimum inhibitory concentration
Assayed by paper disc method using ToYo disc (trade name), on nutrient agar (agar: 1.0%, **0.5%), except on *potato agar.

Antibiotic 81-484 shows antimicrobial activity against some kinds of fungi but does not show any antibacterial activity against Gram positive bacteria.

2. Antitumor activity:

(a) Effect on P388 mouse leukemia:

P388 mouse leukemia, $1 \times 10^5$ cells, were inoculated intraperitoneally into five mice in one group, $CDF_1$, female, age 5 weeks, and the antibiotic as shown in Table 1 was administered to them.

TABLE 1

| Administration (mg/kg/day) | Administ. Day | Life-Span Days (Mean Value) | Life Prolongation Ratio (%) |
| --- | --- | --- | --- |
| Control | — | 12 | 0 |
| 0.016 | 1-5 | 19 | 58 |
| 0.008 | 1-5 | 16 | 33 |

The date of administration was day 0 on the day of tumor inoculation. Each value is the mean value of five mice in one group. The ratio of life prolongation is calculated by the following equation:

$$\text{Ratio of life prolongation (\%)} = \frac{\text{mean value of life} - \text{span days, treated}}{\text{mean value of life} - \text{span days, control}} \times 100 - 100$$

(b) Effect on sarcoma 180:

Sarcoma 180, $1 \times 10^6$ cells, were inoculated intraperitoneally into mice, strain ICR, female, 5 weeks age, and treated as shown in Table 2.

TABLE 2

| Administration (mg/kg/day) | Date of Administ. | Life-Span Days (Mean Value) | Life Prolongation Ratio (%) |
| --- | --- | --- | --- |
| Control | — | 12 | 0 |
| 0.031 | 1-5 | 20 | 67 |
| 0.016 | 1-5 | 28 | 133 |
| 0.008 | 1-5 | 22 | 83 |

The date of administration is day 0 on the day of tumor inoculation. Each value is the mean value of 5 mice in a group and the ratio of life prolongation is calculation by the equation give hereinbefore.

As shown in Tables 1 and 2, the antibiotic 81-484 has antitumor activity against P388 leukemia and sarcoma 180 ascites carcinoma.

Heretofore, antibiotics having properties similar to those of antibiotic 81-484 have been reported as antibiotic ATS-1287 (Jap. Unexam. Pat. Publ. No. 55-118499) and Leptomycin A and B [J. Antibiotics, 36(6), 639-650 (1983)]. However, antibiotic ATS-1287 is different as to specific rotation and NMR spectrum. Leptomycin A and B are different as to molecular formula, specific rotation and NMR spectrum. Therefore, the antibiotic 81-484 is shown to be a novel antibiotic.

The following examples illustrate the present invention, but are not to be construed as limiting.

EXAMPLE 1

Culture of strain 81-484:

A liquid culture medium (pH 7) (medium A) (100 ml×30) in a 500 ml Erlenmeyer flask, consisting of glucose 2.0%, peptone 0.5 ml, meat extract 0.5%, dry yeast 0.3%, NaCl 0.5% and calcium carbonate 0.3%, was sterilized. A loopful of Streptomyces 81-484 FERM-P 7371 cultured on an agar slant medium consisting of glucose 1%, peptone 0.5%, meat extract 0.5%, NaCl 0.3% and agar 1.2% was inoculated thereinto and the medium was shake cultured at 27° C. for 72 hours with an amplitude of 17 cm, 120 reciprocations per minute, to prepare a seed culture.

The seed culture (2.5 lit.) was aseptically inoculated into medium A (120 lit.) in a 200 lit. fermenter, and aerobically cultured to obtain the cultured liquid (approx. 120 lit.)

EXAMPLE 2

Extraction of antibiotic 81-484:

Culture liquid obtained in Example 1 was filtered after adding a filter aid. The filtrate and mycelia wash liquid (120 lit.) were passed through an Amberlite XAD-7 (trade name) column (5 lit.) to adsorb the active principle. The column was washed with water and 20% aqueous ethanol to elute the contaminants, and the active principle was eluted with 40% aqueous ethanol. The eluate (25 lit.) was concentrated in vacuo to appoximately 300 ml and the precipitate was removed by filtration. The concentrate with added ethyl acetate was agitated thoroughly. The separated ethyl acetate layer was dehydrated by adding anhydrous sodium sulfate and concentrated in vacuo to obtain oily antibiotic 81-484 (20 g).

EXAMPLE 3

Purification by silica gel chromatography:

The oily material obtained in Example 2 was charged on a column (46×600 mm) of silica gel 60 (Merck) previously packed with hexane, and eluted with gradiently changed hexane-acetone. The active fractions were concentrated in vacuo, and again adsorbed on a column of silica gel previously packed with hexane, and eluted with gradiently changed hexane-ethyl acetate. The active fractions were concentrated in vacuo to obtain crude antibiotic 81-484 (100 mg, purity 50%).

EXAMPLE 4

Isolation by HPLC:

High performance liquid chromatography (HPLC) [Japan. Spectrophot. TRIROTAR-V, UVIDE-100-V, VL-613, GP-A40] was used for further purification. Octadecylsilane silica gel (Showa Denko Co., Fine SIL $C_{18}$-10) was packed in a stainless steel column (10×250 mm, Showa Denko Co.)

Crude antibiotic 81-484 (1 mg), obtained in Example 3, dissolved in methanol (100 μl) was injected in the column, developed with a mixture of water:methanol (30:70, medium for HPLC) and chromatographed. The peak corresponding to antibiotic 81-484 was collected by detecting at 220 nm UV adsorption. The methanol was distilled off in vacuo and ethyl acetate was added to the residue. The mixture was stirred at acidic pH to transfer the antibiotic into the ethyl acetate layer. The ethyl acetate layer was washed with purified water and dried in vacuo to obtain purified antibiotic 81-484 (400 μg). The same operations were repeated several scores of times to obtain further antibiotic 81-484 (approximately 200 mg).

What is claimed is:

1. Antibiotic 81-484 of the following physico-chemical properties:
   (1) elementary analysis: $C_{33}H_{48}O_7$ (high resolution mass spectrum;
   (2) molecular weight: 556 (Field desorption (FD) mass spectrum;
   (3) melting point: not clear (oily at 10°–100° C.);
   (4) specific rotation: $[\alpha]_D^{20} = -151°$ (c=0.1, methanol);
   (5) ultraviolet absorption spectrum: shown in FIG. 1 (in methanol);
   (6) infrared absorption spectrum: shown in FIG. 2 (KBr tablet);
   (7) solubility:
      insoluble in hexane and water,
      soluble in diethyl ether, methanol, ethanol, dichloromethane, chloroform, ethyl acetate, butyl acetate, acetone and benzene;
   (8) nuclear magnetic resonance spectrum: shown in FIG. 3 ($CDCl_3$, TMS);
   (9) nature: acidic substance;
   (10) color reaction:
      negative for ninhydrin, anthrone-$H_2SO_4$ and ferric chloride reaction;
      positive for iodine and antimony trichloride;
      weakly positive for Zatkis reagent;
   or a pharmacologically acceptable non-toxic salt thereof.

* * * * *

Notice of Adverse Decision in Interference

In Interference No. 102,066, involving Patent No. 4,550,021, I. Umezawa and K. Komiyama, ANTITUMOR ANTIBIOTIC 81-484 AND PROCESS FOR ITS PRODUCTION, final judgment adverse to the patentees was rendered June 6, 1989, as to claim 1.

[*Official Gazette September 19, 1989.*]